United States Patent [19]

Nakagawa

[11] Patent Number: 5,281,407

[45] Date of Patent: Jan. 25, 1994

[54] METHOD FOR PREPARING CRYSTALLINE MATERIALS USING AZA-POLYCYCLIC TEMPLATING AGENTS

[75] Inventor: Yumi Nakagawa, Oakland, Calif.

[73] Assignee: Chevron Research and Technology Company, San Francisco, Calif.

[21] Appl. No.: 907,419

[22] Filed: Jun. 30, 1992

[51] Int. Cl.$^5$ .................. C01B 33/34; B01J 20/18; B01J 29/00
[52] U.S. Cl. ..................... 423/706; 423/328.1; 502/62
[58] Field of Search ............... 423/704, 705, 706, 707, 423/328.1, 328.2; 502/60, 61, 62

[56] References Cited

U.S. PATENT DOCUMENTS

| | | | |
|---|---|---|---|
| 4,285,922 | 8/1981 | Audeh et al. | 423/708 |
| 4,508,837 | 4/1985 | Zones | 423/708 |
| 4,510,256 | 4/1985 | Zones | 423/706 |
| 4,910,006 | 3/1990 | Zones et al. | 423/328 |
| 4,963,337 | 10/1990 | Zones | 423/277 |
| 5,106,801 | 4/1992 | Zones et al. | 502/64 |

Primary Examiner—Carl F. Dees
Attorney, Agent, or Firm—A. W. Klaassen; W. K. Turner

[57] ABSTRACT

Molecular sieves, particularly zeolites, are prepared using templates derived from a 4-azonia-tricyclo[5.2.n.0$^{2,6}$]alkene family of compounds. The templates may be prepared in a series of reaction steps which include a Diels-Alder reaction between a diene and a dienophile.

66 Claims, No Drawings

METHOD FOR PREPARING CRYSTALLINE MATERIALS USING AZA-POLYCYCLIC TEMPLATING AGENTS

BACKGROUND OF THE INVENTION

1. Field of the Invention

The present invention relates to a new method for synthesizing crystalline molecular sieves using a new family of templating agents.

2. Background

The crystalline materials of this invention contain metallic and non-metallic oxides bonded through oxygen linkages to form a three-dimensional structure. Molecular sieves are a commercially important class of crystalline materials. Natural and synthetic crystalline molecular sieves are useful as catalysts and adsorbents. They have distinct crystal structures with ordered pore structures which are demonstrated by distinct X-ray diffraction patterns. The crystal structure defines cavities and pores which are characteristic of the different species. The adsorptive and catalytic properties of each molecular sieve are determined in part by the dimensions of its pores and cavities. Thus, the utility of a particular molecular sieve in a particular application depends at least partly on its crystal structure.

Because of their unique sieving characteristics, as well as their catalytic properties, molecular sieves are especially useful in such applications as gas drying and separation and hydrocarbon conversion. Although many different molecular sieves have been disclosed, there is a continuing need for new materials with desirable properties for gas separation and drying, hydrocarbon and chemical conversions, and other applications.

The term "molecular sieve" refers to a material prepared according to the present invention having a fixed, open-network structure, usually crystalline, that may be used to separate hydrocarbons or other mixtures by selective occlusion of one or more of the constituents, or may be used as a catalyst in a catalytic conversion process.

The term "zeolite" refers to a molecular sieve containing a silicate lattice, usually in association with some alumina, boron, gallium, iron, and/or titanium. In the following discussion, the terms molecular sieve and zeolite will be used more or less interchangeably, since most of the work was carried out on zeolites. However, one skilled in the art will recognize that the teachings relating to zeolites are also applicable to the more general class of materials called molecular sieves.

The term "aluminosilicate" refers to a zeolite containing both framework alumina and framework silica. The term "silicate" refers to a zeolite having a high $SiO_2/Al_2O_3$ mole ratio, preferably a $SiO_2/Al_2O_3$ mole ratio greater than 100. The term "borosilicate" refers to a Zeolite containing both boron and silicon, and having a $SiO_2/B_2O_3$ ratio of greater than 20.

Many different combinations of oxides have been prepared with molecular sieve properties, with silicates, aluminosilicates, and borosilicates being well known examples. Typical aluminosilicate zeolites include zeolite A (U.S. Pat. No. 2,882,243), zeolite X (U.S. Pat. No. 2,882,244), zeolite Y (U.S. Pat. No. 3,130,007), zeolite beta (U.S. Pat. No. 3,308,069), zeolite ZSM-5 (U.S. Pat. No. 3,702,886), ZSM-11 (U.S. Pat. No. 3,709,979), ZSM-12 (U.S. Pat. No. 3,832,449), zeolite ZSM-20 (U.S. Pat. No. 3,972,983), zeolite ZSM-35 (U.S. Pat. No. 4,016,245), zeolite ZSM-38 (U.S. Pat. No. 4,046,859), zeolite ZSM-23 (U.S. Pat. No. 4,076,842), to name a few. Typical crystalline silicates include silicalite (U.S. Pat. No. 4,061,724). Typical borosilicates include SSZ-33 (U.S. Pat. Pat. No. 4,963,337).

Organic templating agents are believed to play an important role in the process of molecular sieve crystallization. Organic amines and quaternary ammonium cations were first used in the synthesis of zeolites in the early 1960,s This approach led to a significant increase in the number of new zeolitic structures discovered as well as an expansion in the boundaries of composition of the resultant crystalline products. Previously, products with low silica to alumina ratios ($SiO_2/Al_2O_3 \leq 10$) had been obtained, but upon using the organocations as components in the starting gels, zeolites with increasingly high $SiO_2/Al_2O_3$ ratios were realized.

Crystalline aluminosilicates are usually prepared from aqueous reaction mixtures containing alkali or alkaline earth metal oxides, silica, and alumina. By varying the synthesis conditions and the composition of the reaction mixture, different zeolites can be formed using the same templating agent.

Compounds having chemical structures which fall outside the scope of the present invention have also been disclosed as templating agents for various crystalline materials. Use of N,N,N-trimethyl cyclopentylammonium iodide in the preparation of Zeolite SSZ-15 molecular sieve is disclosed in U.S. Pat. No 4,610,854; use of 1-azoniaspiro [4.4] nonyl bromide and preparation of a molecular sieve termed "Losod" is disclosed in Hel. Chim. Acta (1974), Vol. 57, page 1533 (W. Sieber and W. M. Meier); use of 1,1ω-di(1-azoniabicyclo [2.2.2.] octane) lower alkyl compounds in the preparation of Zeolite SSZ-16 molecular sieve is disclosed in U.S. Pat. No. 4,508,837; use of N,N,N-trialkyl-1 adamantammonium salts in the preparation of zeolite SSZ-13 molecular sieve is disclosed in U.S. Pat. No. 4,544,538. U.S. Pat. No. 5,053,373 discloses preparing SSZ-32 with an N-lower alkyl-N'-isopropyl-imidazolium cation templating agent. U.S. Pat. No. 5,106,801 discloses a cyclic quaternary ammonium ion, and specifically a tricyclodecane quaternary ammonium ion, for the preparation of the metallosilicate zeolite SSZ-31. U.S. Pat. No. 4,910,006 teaches using a hexamethyl[4.3.3.0]propellane-8,11-diammonium cation for the preparation of SSZ-26. EP 0193282 discloses a tropinium cation for preparing the clathrasil ZSM-58. Similarly, use of quinuclidinium compounds to prepare a zeolite termed "NU-3" is disclosed in European Patent Publication No. 40016.

It is desirable to have a method to make aza-polycyclic, nitrogen-containing ring systems in a deliberate fashion, for use as templates in the synthesis of crystalline materials, where the ring size and position of substituents in the ring can be predicted and controlled. It would also be desirable to accomplish this using inexpensive starting materials.

SUMMARY OF THE INVENTION

This invention provides a novel process for preparing crystalline materials, and more specifically crystalline oxide materials. This process includes contacting active sources of the components of the crystalline materials and an organocationic templating agent. The templating agent is generally derived from a 4-azonia-tricyclo[5.2.n.0$^{2,6}$]alkene family of compounds, wherein each member of the family is a compound which may be prepared via a Diels-Alder reaction pathway.

More specifically, a method is provided for preparing a crystalline material comprising one or a combination of oxides selected from the group consisting of one or more trivalent element(s) and one or more tetravalent element(s), said method comprising contacting under crystallization conditions sources of said oxides and an aza-polycyclic templating agent having a molecular structure of the form:

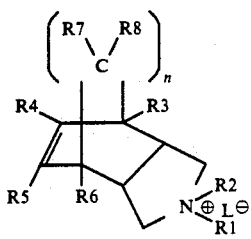

(I)

wherein:
R1 and R2 are each selected from the group consisting of hydrogen, a lower alkyl group, and, when taken together, a spirocyclic group having from 3 to 6 carbon atoms;
R3, R4, R5 and R6 are each selected from the group consisting of hydrogen, halogen, and a lower alkyl group;
n has a value of 1, 2, 3, or 4;
R7 and R8 are each selected from the group consisting of hydrogen and a lower alkyl group, and when n is one (1), R7 and R8 can be taken together to form a spirocyclic group having from 3 to 6 carbon atoms; and, when n is two (2) or greater, one of R7 and R8 on one carbon atom can be taken together with one of R7 and R8 on an adjacent carbon atom to form a ring having from 3 to 6 carbon atoms; and
L is an anion.

Aza-polycyclic compounds encompassed by this formula are hereinafter referred to as the "defined aza-polycyclic templating agents".

The preferred crystalline material is a molecular sieve. The preferred trivalent element is selected from the group consisting of aluminum, boron, gallium, iron, and combinations, with aluminum and/or boron being particularly preferred. The preferred tetravalent element is selected from silicon and germanium, with silicon being particularly s preferred. As used herein, the term "halogen" refers to fluorine, chlorine, bromine, and combinations thereof. The term "lower alkyl group" refers to a linear, branched, or cyclic alkyl group having from 1 to 6 carbon atoms. The term "spirocyclic group" refers to a cyclic group in a polycyclic hydrocarbon having one carbon atom in common with a second cyclic group. L is an anion which is not detrimental to the formation of the molecular sieve. Representative anions include halogens, such as fluoride, chloride, bromide, and iodide, hydroxide, acetate, sulfate, carboxylate. Hydroxide is the most preferred anion. It may be beneficial to ion exchange, for example, the halide for hydroxide ion, thereby reducing or eliminating the alkali metal hydroxide quantity required.

Our invention is also directed to a crystalline material comprising tetrahedrally bound oxide units and the defined aza-polycyclic templating agent, said oxide units comprising one or a combination of trivalent elements and tetravalent elements.

Preferably, the composition comprising oxide units has a molar composition, as synthesized and in the anhydrous state, as follows:

$$aQ:bM_2O:cW_2O_3:100YO_2$$

wherein:
Q is the defined aza-polycyclic templating agent having a molecular structure of the form shown in Structure I above;
M is one or a combination of alkali metal cations and/or alkaline earth metal cations;
W is one or a combination of elements selected from aluminum, boron, gallium, and iron;
Y is one or a combination of elements selected from silicon and germanium;
a has a value in the range of 5 to 50;
b has a value in the range of 0.5 to 100; and
c has a value in the range of 0 to 10.

Among other factors, we have discovered that small changes in structure within this family of relatively rigid, polycyclic templating agents, when the template is used in molecular sieve synthesis, can lead to significant changes in the crystalline molecular sieve formed. In particular, this family of templates (prepared via a Diels-Alder route) can be used to make several catalytically interesting large-pore zeolites under a variety of reaction conditions.

DETAILED DESCRIPTION OF THE INVENTION

In preparing a crystalline material according to the present invention, a defined aza-polycyclic compound, having a general molecular structure of the form shown in Structure I above, acts as a template or structure directing agent during the crystallization. In another embodiment of the invention, the defined aza-polycyclic templating agent is prepared in a series of reaction steps comprising a Diels-Alder reaction between a diene and a dienophile. In another embodiment is the molecular sieve, as prepared and comprising the defined aza-polycyclic templating agent.

Crystalline zeolites which may be prepared according to the present process include ZSM-12, ZSM-48, SSZ-13, SSZ-15, SSZ-24, SSZ-31, SSZ-33, SSZ-37, zeolite beta, and other similar materials. New crystalline molecular sieve structures may result as well by the present method.

In the method of this invention the family of aza-polycyclic cations can be used to synthesize different zeolitic materials depending on the reagents, reactant ratios and reaction conditions. For example, factors which may affect the crystallization of a given zeolite include the specific defined aza-polycyclic template used, the type and ratio of inorganic reagents used, the concentration of alkali metal relative to the metal oxide concentrations, temperature, and time.

The full scope of the composition and process of the present invention will be apparent to those familiar with crystalline molecular sieves and their methods of preparation from the following detailed description of the principal features of the composition and from the examples which accompany the description.

Templating Agent

The templating agent useful in the present process is generally derived from the 4-azoniatricyclo[5.2.n.0$^{2,6}$]alkene family of compounds, where n is a number and has a value of 1, 2, 3, or 4. The templating agent has a molecular structure of the general form:

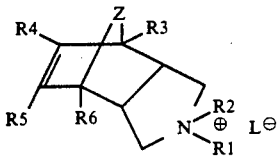

wherein

Z is selected from the group consisting of oxygen, nitrogen, sulfur, and an alkyl radical:

R1 and R2 are each selected from the group consisting of hydrogen, a lower alkyl group, and, when taken together, a spirocyclic group having from 3 to 6 carbon atoms;

R3, R4, R5 and R6 are each selected from the group consisting of hydrogen, halogen, and a lower alkyl group; and L is an anion.

In a further embodiment, the templating agent has a molecular structure of the form:

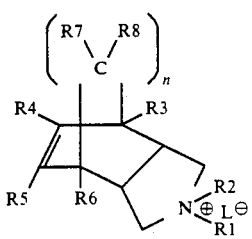

(I)

wherein:

R1, R2, R3, R4, R5, and R6 are radicals as defined above;

n has a value of 1, 2, 3, or 4; and

R7 and R8 are each selected from the group consisting of hydrogen, and a lower alkyl group, and when n is one (1), R7 and R8 can be taken together to form a spirocyclic group having from 3 to 6 carbon atoms; and, when n is two (2) or greater, one of R7 and R8 on one carbon atom can be taken together with one of R7 and R8 on an adjacent carbon atom to form a ring having from 3 to 6 carbon atoms.

Preferably, R1 and R2 are each selected from the group consisting of hydrogen, an alkyl group having from 1 to 3 carbon atoms, and, when taken together, a spirocyclic group having from 3 to 6, more preferably from 4 to 5, carbon atoms.

Preferably, R3, R4, R5 and R6 are each selected from the group consisting of hydrogen, halogen, and an alkyl group having from 1 to 3 carbon atoms.

Preferably, R7 and R8 are each selected from the group consisting of hydrogen and an alkyl group having from 1 to 3 carbon atoms, and when n is one (I), R7 and R8 can be taken together to form a spirocyclic group having from 3 to 6, more preferably from 3 to 5, carbon atoms; and, when n is two (2) or greater, one of R7 and R8 on one carbon atom can be taken together with one of R7 and R8 on an adjacent carbon atom to form a ring having from 3 to 6, more preferably from 3 to 5, carbon atoms.

In particular, each member of the family has a charged nitrogen heteroatom and a bridging structure forming a multiplicity of rings.

Many of the organocations which have been previously used as templates for molecular sieve synthesis are conformationally flexible. These molecules adopt many conformations in aqueous solution, and several templates can give rise to a single crystalline product. In contrast, the defined azapolycyclic templating agents used in the present invention are conformationally rigid organic molecules. Altering the structure of these rigid molecules can lead to a change in the molecular sieve obtained, presumably due to the differing steric demands of each template. In particular, we have found that the present templating agent is useful for synthesizing large pore zeolites, which are important for catalytic applications.

However, increasing the steric demand of the template may lead to a decrease in crystallization rate as well as a decrease in template solubility in the reaction mixture. If the template is not sufficiently soluble, it will be difficult to form crystals in the reaction mixture. Addition of a surfactant to the reaction mixture may help to solubilize the template.

Employing a Diels-Alder reaction scheme, using inexpensive reagents, is the preferred method for preparing the present templating agents. The Diels-Alder reaction is one of the most useful transformations in synthetic organic chemistry. Two new bonds and a six-membered ring are formed in the Diels-Alder reaction, formally a [4+2]cycloaddition of a 1,4-conjugated diene with a double bond (dienophile). The dienophile may include a carbon-carbon, carbon-heteroatom, or heteroatom-heteroatom double (or triple) bond, leading to a diverse pool of potential templating agents. Electron-withdrawing groups on the dienophile greatly increase its reactivity, whereas electron-donating groups on the diene have the same effect. The Diels-Alder reaction is discussed in greater detail in F. Fringuelli and A. Taticchi, Dienes in the Diels-Alder Reaction 1990, J. Wiley and Sons, Inc.

The versatility of the Diels-Alder reaction is in part responsible for its usefulness. A wide range of starting materials are available, making possible the preparation of numerous products. The stereoelectronics of the reaction, as well as its concerted nature, often allows one to predict which product will be formed if several are possible. Therefore, by the proper choice of starting materials, very efficient syntheses of target templates can be achieved.

In particular, the Diels-Alder reaction pathway provides a method for synthesizing the defined aza-polycyclic ring systems which are useful in the present process. Varying either the diene or the dienophile produces small but significant structural changes to the key intermediates in the synthesis.

The dienes useful for preparing the defined aza-polycyclic templates are of the following general form:

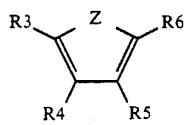

wherein:

Z is selected from the group consisting of oxygen, nitrogen, sulfur, and an alkyl radical; and R3, R4, R5 and R6 are each selected from the group consisting of hydrogen, halogen, and a lower alkyl group.

In a further embodiment, the dienes useful for preparing the defined aza-polycyclic templates have the following form:

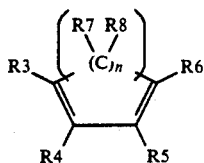

(II)

wherein:

n has a vague of 1, 2, 3, or 4;

R3, R4, R5, and R6 are as described above; and

R7 and R8 are each selected from the group consisting of hydrogen, and a lower alkyl group, and when n is one (1), R7 and R8 can be taken together to form a spirocyclic group having from 3 to 6 carbon atoms; and, when n is two (2) or greater, one of R7 and R8 on one carbon atom can be taken together with one of R7 and R8 on an adjacent carbon atom to form a ring having from 3 to 6 carbon atoms.

Preferably, R3, R4, R5 and R6 are each selected from the group consisting of hydrogen, halogen, and an alkyl group having from 1 to 3 carbon atoms.

Preferably, R7 and R8 are each selected from the group consisting of hydrogen and an alkyl group having from 1 to 3 carbon atoms, and when n is one (1), R7 and R8 can be taken together to form a spirocyclic group having from 3 to 6, more preferably from 3 to 5, carbon atoms; and, when n is two (2) or greater, one of R7 and R8 on one carbon atom can be taken together with one of R7 and R8 on an adjacent carbon atom to form a ring having from 3 to 6, more preferably from 3 to 5, carbon atoms.

Examples of cyclic dienes having a carbon backbone include cyclopentadiene, 1,3-cyclohexadiene, 1,3-cycloheptadiene, 1,3-cycloheptatriene, spiro[2,4]hepta-4,6-diene, and 1,3-cyclooctadiene. The diene of structure II may also include one or more heteroatoms in the cyclic backbone, including oxygen, nitrogen, and/or sulfur. Oxygen is preferred. Non-limiting examples of heterodienes which are used in preparing the templating agent include furan, pyrrol, and thiophene. Examples of functional groups R7 and R8 in structure II are hydrogen, methyl, ethyl, propyl, and cyclopropyl.

The dienophile from which the present templating agent is prepared has a structure of the general form:

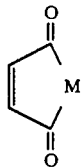

(III)

wherein M is either oxygen or nitrogen having a substituent group selected from the group consisting of hydrogen and a lower alkyl group.

Our defined aza-polycyclic compounds are prepared by methods known in the art. The reactions involved are described in detail in, for example, Chem. Pharm. Bull. (1962), 10, 714-718, L. F. Fieser and M. Fieser, 1967, Reagents for Organic Synthesis, vol 1, pp. 581-594, New York: J. Wiley and Sons, Inc. and W. K. Anderson and A. S. Milowsky, 1985, J. Org. Chem. 50,5423-24. when a diene, such as that shown in structure II above, is reacted with a dienophile such as that shown in structure III, wherein element M is oxygen, the resulting product is reacted with an amine to form an imide, then reduced to the corresponding pyrrolidine using a reducing agent such as lithium aluminum hydride, and then quaternized with, for example methyl iodide, to form the defined aza-polycyclic templating agent.

When the diene of structure II above, is reacted with a dienophile of structure III, wherein element M is nitrogen having a lower alkyl substituent group, the resulting imide product is directly reduced to the corresponding pyrrolidine and then quaternized to form the cationic templating agent.

The double bond shown in Structure I above is not critical to the action of the defined aza-polycyclic compound as a templating agent, and may be reduced, using techniques readily available in the art, such as, for example, by reaction over a palladium/carbon or a platinum/carbon catalyst in the presence of hydrogen. The reduced compound will also serve as a templating agent in the present method.

Crystalline Materials of this Invention

The crystalline materials of this invention comprise the templating agent in combination with metallic and non-metallic oxides bonded in tetrahedral coordination through shared oxygen atoms to form a cross-linked three dimensional crystal structure. The metallic and non-metallic oxides comprise one or a combination of oxides selected from the group consisting of one or more trivalent element(s) and one or more tetravalent element(s). The trivalent element is preferably selected from the group consisting of aluminum, boron, gallium, iron, and combinations thereof. More preferably, the trivalent element is selected from the group consisting of aluminum and boron. The tetravalent element is selected from the group consisting of silicon, germanium, and combinations thereof. More preferably, the tetravalent element is silicon.

The crystalline material comprises one or a combination of oxides, said oxides being selected from a range of metal oxidation states. The crystalline material also contains a defined aza-polycyclic templating agent having the molecular structure of the form shown in Structure I above. The entire lattice is charged balanced.

Preferably, the crystalline material has a molar composition, as synthesized and in the anhydrous state, as follows:

$$aQ:bM_2O:cW_2O_3:100YO_2$$

wherein:

Q is the defined aza-polycyclic templating agent having a molecular structure of the form shown in Structure I above;

M is one or a combination of alkali metal cations and/or alkaline earth metal cations;

W is one or a combination of elements selected from aluminum, boron, gallium, and iron;

Y is one or a combination of elements selected from silicon and germanium;
a has a value in the range of 5 to 50;
b has a value in the range of 0.5 to 100; and
c has a value in the range of 0 to 10.

The crystalline materials can be suitably prepared from an aqueous solution containing sources of at least one templating agent of this invention, and at least one oxide capable of forming a crystalline molecular sieve. Examples of a suitable metal oxide include an alkali metal oxide, and oxides of aluminum, silicon, boron, germanium, iron, gallium, and the like.

The present process is suitable for preparing aluminosilicate zeolites from a reaction mixture prepared using standard zeolitic preparation techniques. Typical sources of aluminum oxide for the reaction mixture include aluminates, alumina, and aluminum compounds such as $AlCl_3$, hydrated $Al(OH)_3$ gels and $Al_2(SC_4)_3$. Typical sources of silicon oxide include silicates, silica hydrogel, silicic acid, colloidal silica, tetra-alkyl orthosilicates, and silica hydroxides. Gallium, germanium, iron, and boron can be added in forms corresponding to their aluminum and silicon counterparts.

Alternatively a source zeolite reagent, such as zeolite A, zeolite X, zeolite Y, and zeolite rho, may provide a source of alumina for the present process. In some cases, the source zeolite may also provide a source of silica and/or boron. Alternatively, the source zeolite in its dealuminated forms may be used as a source of alumina and silica, with additional silicon added using, for example, the conventional sources listed above.

Typically, an alkali metal hydroxide and/or an alkaline earth metal hydroxide, such as the hydroxide of sodium, potassium, lithium, cesium, rubidium, calcium, and magnesium, is used in the reaction mixture; however, this component can be omitted so long as the equivalent basicity is maintained. The templating agent may be used to provide hydroxide ion. The alkali metal cation or alkaline earth cation may be part of the as-synthesized crystalline oxide material, in order to balance valence electron charges therein.

The present process is suitable for preparing silicates or "essentially alumina-free" zeolites, i.e., a product having a silica to alumina mole ratio of $\infty$. The term "essentially alumina-free" is used because it is difficult to prepare completely aluminum-free reaction mixtures for synthesizing these materials. Especially when commercial silica sources are used, aluminum is almost always present to a greater or lesser degree. The hydrothermal reaction mixtures from which the essentially alumina-free crystalline siliceous molecular sieves may be prepared can be referred to as being substantially alumina free. By this usage is meant that no aluminum is intentionally added to the reaction mixture, e.g., as an alumina or aluminate reagent, and that to the extent aluminum is present, it occurs only as a contaminant in the reagents. An additional method of increasing the mole ratio of silica to alumina is by using standard acid leaching or chelating treatments.

In preparing the crystalline material under crystallization conditions according to the present invention, the reaction mixture is maintained at an elevated temperature until crystals are formed. The temperatures during the hydrothermal crystallization step are typically maintained from about 100° C. to about 235° C., preferably from about 120° C. to about 200° C. The crystallization period is typically greater than 1 day and preferably from about 3 days to about 50 days.

The hydrothermal crystallization is usually conducted under pressure and usually in an autoclave so that the reaction mixture is subject to autogenous pressure. The reaction mixture can be stirred during crystallization.

Once the crystals have formed, the solid product is separated from the reaction mixture by standard mechanical separation techniques, such as filtration. The crystals are water-washed and then dried, e.g., at 90° C. to 150° C. for from 8 to 24 hours, to obtain the synthesized zeolite crystals. The drying step can be performed at atmospheric or subatmospheric pressures.

During the hydrothermal crystallization step, the crystals can be allowed to nucleate spontaneously from the reaction mixture. The reaction mixture can also be seeded with crystals both to direct, and accelerate the crystallization, as well as to minimize the formation of undesired aluminosilicate contaminants. If the reaction mixture is seeded with crystals, the concentration of the defined azapolycyclic template may sometimes be somewhat reduced.

Due to the unpredictability of the factors which control nucleation and crystallization in the art of crystalline oxide synthesis, not every combination of reagents, reactant ratios, and reaction conditions will result in crystalline products. Selecting crystallization conditions which are effective for producing crystals may require routine modifications to the reaction mixture composition or to the reaction conditions, such as temperature and/or crystallization time. Making these modifications are well within the capabilities of one skilled in the art.

The crystalline material, more specifically the synthetic molecular sieve or zeolite, can be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica alumina mole ratio. The zeolite can also be steamed; steaming helps stabilize the crystalline lattice to attack from acids. The zeolite can be used in intimate combination with hydrogenating components, such as tungsten, vanadium molybdenum, rhenium, nickel cobalt, chromium, manganese, or a noble metal, such as palladium or platinum, for those applications in which a hydrogenation-dehydrogenation function is desired. Typical replacing cations can include metal cations, e.g., rare earth, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

Zeolite ZSM-12 and the conventional preparation thereof are described in U.S. Pat. No. 3,832,449, the disclosure of which is incorporated herein by reference. Zeolite beta and the conventional preparation thereof are described in U.S. Pat. No. 3,308,069, the disclosure of which is incorporated herein by reference. Zeolite SSZ-13 and the conventional preparation thereof are described in U.S. Pat. No. 4,544,538, the disclosure of which is incorporated herein by reference. Zeolite SSZ-15 is a version of the crystalline oxide Nonasil. Zeolite SSZ-15 and the conventional preparation thereof are described in U.S. Pat. No. 4,610,854, the disclosure of which is incorporated herein by reference. Zeolite SSZ-31 and the conventional preparation thereof are described in U.S. Pat. No. 5,106,801, the disclosure of which is incorporated herein by reference. Zeolite SSZ-33 and the conventional preparation thereof are described in U.S. Pat. No. 4,963,337, the disclosure of which is incorporated herein by reference. Zeolite SSZ-37 and the preparation thereof is described in concurrently filed U.S. Ser. No. 07/906,919, entitled "NEW ZEOLITE SSZ-37", by Y. Nakagawa, the disclosure of which is incorporated herein by reference.

The hydrogen, ammonium, and metal components can be exchanged into the zeolite. The zeolite can also be impregnated with the metals, or, the metals can be physically intimately admixed with the zeolite using standard methods known to the art. And the metals can be occluded in the crystal lattice by having the desired metals present as ions in the reaction mixture from which the zeolite is prepared.

Typical ion exchange techniques involve contacting the synthetic zeolite with a solution containing a salt of the desired replacing cation or cations. Although a wide variety of salts can be employed, chlorides and other halides, nitrates, and sulfates are particularly preferred. Representative ion exchange techniques are disclosed in a wide variety of patents including U.S. Pat. Nos. 3,140,249; 3,140,251; and 3,140,253. Ion exchange can take place therefore before or after the zeolite is calcined.

Following contact with the salt solution of the desired replacing cation, the zeolite is typically washed with water and dried at temperatures ranging from 65° C. to about 315° C. After washing, the zeolite can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of the zeolite, the spatial arrangement of the atoms which form the basic crystal lattice of the zeolite remains essentially unchanged. The exchange of cations has little, if any effect on the zeolite lattice structures.

The molecular sieve can be formed into a wide variety of physical shapes. Generally speaking, the zeolite can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or, dried or partially dried and then extruded.

The zeolite can be composited with other materials resistant to the temperatures and other conditions employed in organic conversion processes. Such matrix materials include active and inactive materials and synthetic or naturally occurring Zeolites as well as inorganic materials such as clays, silica and metal oxides. The latter may be naturally occurring or may be in the form of gelatinous precipitates, sols, or gels, including mixtures of silica and metal oxides. Use of an active material in conjunction with the synthetic zeolite, combined with it, can improve the conversion and selectivity of the catalyst in certain organic conversion processes. Inactive materials can serve as diluents to control the amount of conversion in a given process so that products can be formed economically without using other means for controlling the rate of reaction. Frequently, zeolite materials have been incorporated into naturally occurring clays, e.g., bentonite and kaolin. These materials, i.e., clays, oxides, etc., function, in part, as binders for the catalyst. It is desirable to provide a catalyst having good crush strength and attrition resistance, because in petroleum refining the catalyst is often subjected to rough handling. This tends to break the catalyst down into powders which cause problems in processing.

Naturally occurring clays which can be composited with the synthetic zeolites of this invention include the montmorillonite and kaolin families, which families include the sub-bentonites and the kaolins commonly known as Dixie, McNamee, Georgia and Florida clays or others in which the main mineral constituent is halloysite, kaolinite, dickite, nacrite, or anauxite. Various clays such as sepiolite and attapulgite can also be used as supports. Such clays can be used in the raw state as originally mined or can be calcined, treated with acid, or chemically modified.

In addition to the foregoing materials, the zeolite can be composited with porous matrix materials and mixtures of matrix materials such as silica, alumina, titania, magnesia, silica-alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia and silica-magnesia-zirconia. The matrix can be in the form of a cogel.

The zeolite can also be composited with other zeolites such as synthetic and natural faujasites (e.g., X and Y), erionites, and mordenites. They can also be composited with purely synthetic zeolites. The combination of zeolites can also be composited in a porous inorqanic matrix.

The following examples demonstrate but do not limit the is present invention.

EXAMPLES

Examples 1-11 show that one can make a wide range of templates using this methodology. In each of examples 1-11, the anion L may be either I$^-$ or OH$^-$.

Example 1

Diels-Alder adduct

The diene cyclopentadiene was obtained by cracking dicyclopentadiene in a 1-L round bottomed flask fitted with a 30-cm Vigreux column, following the procedure in R. B. Moffett, 1963, Organic Syntheses Coll. Vol IV, ed. N. Rabjohn, pp. 238-241, New York: J. Wiley and Sons, Inc. The cyclopentadiene product was distilled from the cracking vessel and recovered. A 2-L, 3-necked flask was equipped with a magnetic stir bar, reflux condenser and thermometer. The flask was charged with cyclopentadiene (295 g, 4.46 mol) and benzene (1.4 L). The dienophile N-Methylmaleimide (30.1 q, 0.45 mol) was added at room temperature (exotherm noted), and the homogeneous yellow solution was heated to reflux for 24 hours. Thin layer chromatography (silica, 40% ethyl acetate/hexane) was used to monitor the disappearance of maleimide. The reaction mixture was concentrated by rotary evaporation to yield a mixture of oil and solid products, which was taken up in 200 mL of CH$_2$Cl$_2$ and transferred to a separatory funnel. Water (200 mL) was added and the pH of the aqueous layer adjusted to $\leq$1 using conc. HCl. The phases were separated and the organic phase was washed once more with H$_2$O (200 mL). After drying over MgSO$_4$, the organic phase was filtered and concentrated to yield an oil and solid mixture which was recrystallized from 500 mL of hot Et₂O. The ethereal solution was placed in the refrigerator overnight and the resulting white crystals of the Diels-Alder imide were collected by vacuum filtration and washed with a small amount of cold ether (65.43 g, 82% yield, mp 103°-105° C.).

Reduction of Diels-Alder imide

A 3-L, 3-necked flask was fitted with a mechanical stirrer, addition funnel and reflux condenser. The Diels-Alder imide (61.5 g, 0.35 mol) was dissolved in 495 mL of CH₂Cl₂ in the addition funnel. The flask was charged with LiAlH₄ (41.6 g, 1.04 mol) and an anhydrous Et₂O (990 mL) and the system was placed under N₂. The imide solution was added slowly to the LiAlH₄ suspension. Gas evolution and an exotherm were noted. Addition of the imide solution was complete after approx. 1 hour and the grey heterogenous solution was allowed to stir under N₂ overnight. Thin layer chromatography (silica plates, 5% MeOH/95% CH₃Cl) indicated the absence of starting material. The reaction was carefully worked up in the following manner: 38.5 mL of H₂O was added slowly to the reaction. Vigorous gas evolution was noted as well as an exotherm. This step was followed by the cautious addition of 38.5 mL of 15% aqueous NaOH solution. Another 115 mL of H₂O was added and the mixture, which turned from grey to white, was stirred for 1 hour at room temperature. The solids were removed by filtration and washed with CH₂Cl₂. The aqueous layer was acidified with conc. HCL to pH≦1 and the non-basic organic impurities removed in the organic phase. The aqueous layer was then made basic (pH≦12) with 50% NaOH and the crude tertiary amine was isolated by extracting twice with CH₂Cl₂. The organic layers were combined and dried over MgSO₄. Following filtration, the solution was concentrated to yield 41.4 g (52%) of the amine, which was taken directly to the next step. IR and ¹³C NMR spectroscopy could be used to monitor the disappearance of the imide functionality (1700 cm⁻¹ and 177.5 ppm, respectively).

Quaternization of the 4-Methyl-4-aza-tricyclo[5.2.1.0]dec-8-ene

The amine (15.0 g, 0.10 mol) was dissolved in 100 mL of CHCl₃ in a 250-mL round-bottomed flash which was equipped with an addition funnel and magnetic stirrer. The reaction flask was immersed in an ice bath and the addition funnel charged with CH₃I (28.7 g, 0.20 mol). The CH₃I was added to the amine over a 10-minute period (exothermic reaction) and the homogeneous solution was stirred at room temperature for 3 days. Diethyl ether (100 mL) was added to the reaction mixture and the yellow solids were collected by filtration and washed with more ether. These solids were recrystallized from hot acetone/Et₂O (a small amount of MeOH was added to aid in dissolution of solid) to afford 21.2 g of an aza-polycyclic compound having an iodide anion. Bio-Rad AG1-X8 anion exchange resin was used to convert the iodide salt to the corresponding hydroxide form in 90.5% yield. The yield of the conversion was based upon titration of the resultant solution using phenophthalein as the indicator.

The aza-polycyclic templating agent of Example 1 had the structure shown below.

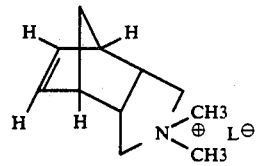

(IV)

Example 2

Example 1 was repeated, except N-ethylmaleimide was used as the dienophile and CH₃CH₂I was used instead of CH₃I in the quaternization step. The resulting product had the structure of structure V below, with the alkyl groups surrounding the positively charged nitrogen being ethyl rather than methyl.

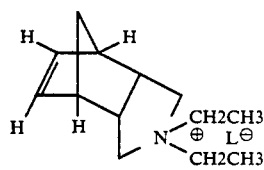

(V)

Example 3

Example 2 was repeated, except CH₃I was used in the quaternization step, giving a cationic templating agent structure VI.

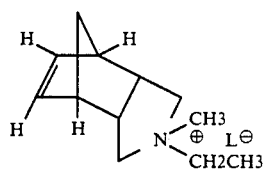

(VI)

Example 4

Example 1 was repeated, except spiro[2.4]hepta-4,6-diene was used as the diene; AlCl₃ was used as a Lewis acid, and the reaction was not heated. In the resulting structure VII the bridging carbon is part of a spirocyclic cyclopropyl group.

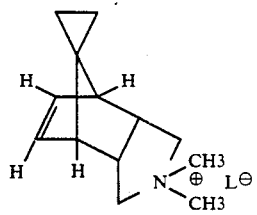

(VII)

Example 5

Example 4 was repeated, except N-ethylmaleimide was used as the dienophile and CH₃CH₂I was used instead of CH₃I in the quaternization step, to give Structure VIII.

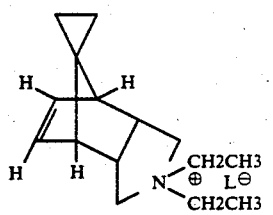

(VIII)

Example 6

Example 1 was repeated, except 1,3-cyclohexadiene was used as the diene and toluene was used as the solvent. In the resulting structure IX the bridging radical has been expanded from one to two carbon atoms.

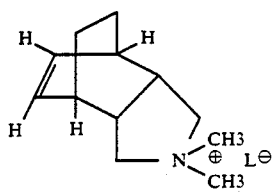

(IX)

Example 7

Example 6 was repeated, except N-ethylmaleimide was used as the dienophile and $CH_3CH_2I$ was used instead of $CH_3I$ in the quaternization step to give Structure X.

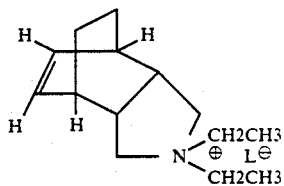

(X)

Example 8

Example 7 was repeated, except $CH_3I$ was used in the quaternization step to give Structure XI.

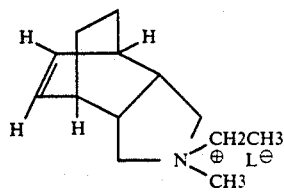

(XI)

Example 9

Example 6 was repeated, except 1-3,cycloheptadiene was used as the diene, and the reaction was heated for four (4) days to give Structure XII.

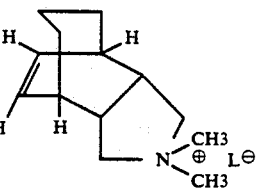

(XII)

Example 10

Example 9 was repeated, except $CH_3CH_2I$ was used instead of $CH_3I$ in the quaternization step to give Structure XIII.

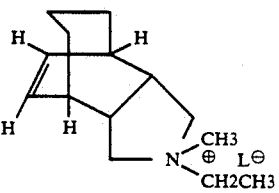

(XIII)

Example 11

Example 6 was repeated, except cycloheptatriene was used as the diene to give Structure XIV.

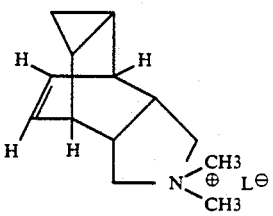

(XIV)

Examples 12–18 illustrate using templates of this invention under a variety of inorganic conditions to obtain zeolitic products. Examples 12 and 16 show that for a given set of inorganic reaction conditions, a minor change in the template structure results in obtaining a different crystalline material. These non-limiting examples illustrate preferred conditions of the invention.

It can be seen that one of the desirable features of this invention is that a wide variety of large pore zeolites can be prepared. As is the case in most molecular sieve syntheses, a given template may not necessarily produce a crystalline product or a single molecular sieve over all inorganic composition ranges.

Example 12: All-silica reaction 1.5 mmol of template of Example 1 as the hydroxide salt, $H_2O$ (7.93 g total in reaction), and 1.0 g 1.0N KOH were added to a teflon cup of a Parr 4745 reactor. Cabosil M-5 (0.62 g, 10 mmol $SiO_2$) was then added to the reaction and the mixture was stirred until it was homogenous. The reaction was heated to 160° C. and tumbled at a rate of 45 rpm. After 6 days, the reaction was filtered, washed with water, and dried to yield a product, determined by XRD to be Nonasil.

Example 13: Boron-containing reaction 1.5 mmol of template of Example 3 as the hydroxide salt, $H_2O$ (7.93 g total in reaction), and 1.3 g 1.0N NaOH were added to a teflon cup of a Parr 4745 reactor. Sodium borate (0.038 g, 0.1 mmol) was added and the mixture was stirred until the sodium borate dissolved. Cabosil M-5 (0.62 g, 10 mmol SiO$_2$) was added and the mixture stirred until it was homogeneous. The reaction was heated to 160° C. and tumbled at a rate of 45 rpm. After 12 days the reaction was filtered, washed with water, and dried to give a product, determined by XRD to ZSM-12, a 12-ring zeolite. In this example boron was found to be incorporated in the final product.

Example 14: Aluminum containing reaction 1.5 mmol of template of Example 2 as the hydroxide salt, H$_2$O (11.89 g total in reaction), and 1.0 g of 1.0N NaOH were added to a teflon cup of a Parr 4745 reactor. Reheis F2000 (0.0195 g, 0.10 mmol Al$_2$O$_3$) was added to the reaction solution which was stirred until the Reheis completely dissolved. Cabosil M-5 (0.62 g, 10 mmol SiO$_2$) was next added to the reaction (giving a starting gel with a SiO$_2$/Al$_2$O$_3$ of 100) and the mixture was stirred until it was homogeneous. The reaction was heated to 160° C. and tumbled at a rate of 43 rpm. After 9 days, the reaction was filtered, washed with water, and dried to give a product, determined by XRD to be ZSM-12. In this example aluminum was found to be incorporated in the final product.

Example 15: Aluminum containing reaction 3.0 mmol of template of Example 6 of the template as the hydroxide salt, water (7.3 g total in the reaction), 0.76 g of 1.0N NaOH were added to a teflon cup of a Parr 4745 reactor. 0.74 grams of Cabosil M5 was blended into the solution, followed by the addition of 0.253 g of a Y zeolite prepared according to U.S. Pat. No. 4,503,023 and U.S. Pat. No. 4,711,773. The starting gel in this case had a SiO$_2$/Al$_2$O$_3$ of 67. The reaction was heated to 160° C. and rotated at 43 rpm on a spit in a Blue M oven. After 20 days a product was obtained, which was filtered, washed with water, dried and determined by XRD to be SSZ-37, a novel zeolitic structure with large pores.

Example 16: All-silica reaction

A reaction was set up and run as in Example 12 except that the template of Example 4 as the hydroxide salt was used as the template. After 14 days, a product was obtained which was filtered, washed with water and determined by XRD to be SSZ-31, a large-pore zeolite.

Example 17: All-silica reaction 2.0 mmole of template of Example 9 as the hydroxide salt, water (7.3 g total in the reaction), 0.50 grams 1.0N KOH and 0.62 grams of Cabosil M5 were mixed together in a teflon cup of a Parr 4745 reactor. The reaction was heated to 160° C. in a Blue M oven for 50 days, after which the gel-like product was filtered, washed with water, dried and determined by XRD to be the large pore zeolite SSZ-24 with a minor amount of amorphous material and a trace of layered material.

Example 18: Boron-containing reaction 2.25 mmole of template of Example 6 as the hydroxide salt, water (11.89 g total in the reaction), 1.95 grams of 1.0N NaOH and 0.057 grams of sodium borate decahydrate (0.15 mmol) were mixed in a teflon cup of a Parr 4745 reactor. 0.93 grams of Cabosil M5 was blended into the reaction and the mixture was heated to 160° C. and tumbled at a rate of 43 rpm for 24 days, after which a settled product was obtained. The solids were filtered, washed with water, dried and determined by XRD to be SSZ-33, another large pore zeolite.

What is claimed is:

1. A method of preparing a crystalline material comprising sources of one or a combination of oxides selected from the group consisting of one or more trivalent element(s) and one or more tetravalent element(s), said method comprising contacting under crystallization conditions said oxides and a templating agent having a molecular structure of the form:

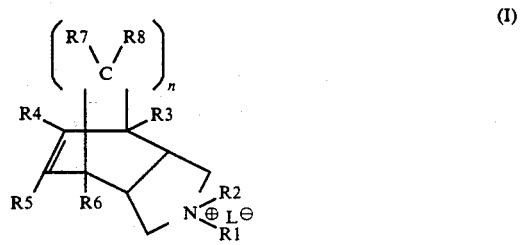

wherein:

R1 and R2 are each selected from the group consisting of hydrogen, a lower alkyl group, and, when taken together, a spirocyclic group having from 3 to 6 carbon atoms;

R3, R4, R5 and R6 are each selected from the group consisting of hydrogen, halogen, and a lower alkyl group;

n has a value of 1, 2, 3, or 4;

R7 and R8 are each selected from the group consisting of hydrogen, and a lower alkyl group, and when n is one (1), R7 and R8 can be taken together to form a spirocyclic group having from 3 to 6 carbon atoms; and, when n is two (2) or greater, one of R7 and R8 on one carbon atom can be taken together with one of R7 and R8 on an adjacent carbon atom to form a ring having from 3 to 6 carbon atoms; and L is an anion.

2. The method according to claim 1 wherein halogen is selected from the group consisting of fluorine, chlorine, bromine and combinations thereof.

3. The method according to claim 1 wherein R1 and R2 are each selected from the group consisting of hydrogen, an alkyl group having from 1 to 3 carbon atoms, and, when taken together, a spirocyclic group having from 4 to 5 carbon atoms.

4. The method according to claim 1 wherein R3, R4, R5 and R6 are each selected from the group consisting of hydrogen and an alkyl group having from 1 to 3 carbon atoms.

5. The method according to claim 1 wherein R7 and R8 are each selected from the group consisting of hydrogen, and an alkyl group having from 1 to 3 carbon atoms, and when n is one (1), R7 and R8 can be taken together to form a spirocyclic group having from 3 to 6 carbon atoms; and, when n is two (2) or greater, one of R7 and R8 on one carbon atom can be taken together with one of R7 and R8 on an adjacent carbon atom to form a ring having from 3 to 6 carbon atoms.

6. The method according to claim 1 wherein the templating agent has a molecular structure of the form:

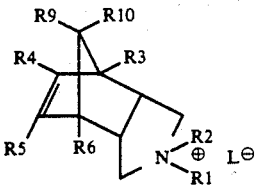

wherein:

R1 and R2 are each selected from the group consisting of hydrogen, a lower alkyl group, and, when taken together, a spirocyclic group having from 3 to 6 carbon atoms;

R3, R4, R5 and R6 are each selected from the group consisting of hydrogen, halogen, and a lower alkyl group;

R9 and R10 are each selected from the group consisting of hydrogen, a lower alkyl group, and, when taken together, a spirocyclic group having from 3 to 6 carbon atoms; and L is an anion.

7. The method according to claim 6 wherein R1 and R2 are selected from the group consisting of hydrogen, an alkyl group having from 1 to 3 carbon atoms, and, when taken together, a spirocyclic group having from 4 to 5 carbon atoms.

8. The method according to claim 6 wherein R3, R4, R5 and R6 are each selected from the group consisting of hydrogen and an alkyl group having from 1 to 3 carbon atoms.

9. The method according to claim 6 wherein R9 and R10 are each selected from the group consisting of hydrogen, an alkyl group having from 1 to 3 carbon atoms, and, when taken together, a spirocyclic group having from 3 to 6 carbon atoms.

10. The method according to claim 6 wherein R3, R4, R5, R6, R9, and R10 are the same and each is hydrogen.

11. The method of claim 10 wherein R1 and R2 are the same and each is methyl.

12. The method according to claim 10 wherein R1 is methyl, R2 is ethyl.

13. The method according to claim 10 wherein R1 and R2 are the same and each is ethyl.

14. The method according to claim 6 wherein R1 and R2 are the same and each is methyl, and R3, R4, R5, and R6, are the same and each is hydrogen, and R9 and R10 are taken together to form a spirocyclic cyclopropane ring.

15. The method according to claim 14 wherein R1 and R2 are the same and each is ethyl.

16. The method according to claim 1 wherein the templating agent has a molecular structure of the form:

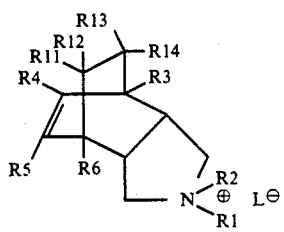

wherein:

R1 and R2 are each selected from the group consisting of hydrogen, a lower alkyl group, and, when taken together, a spirocyclic group having from 3 to 6 carbon atoms;

R3, R4, R5 and R6 are each selected from the group consisting of hydrogen, halogen, and a lower alkyl group;

R11, R12, R13, and R14 are each selected from the group consisting of hydrogen, and a lower alkyl group; and L is an anion.

17. The method according to claim 16 wherein R1 and R2 are selected from the group consisting of hydrogen, an alkyl group having from 1 to 3 carbon atoms, and, when taken together, a spirocyclic group having from 4 to 5 carbon atoms.

18. The method according to claim 16 wherein R3, R4, R5 and R6 are each selected from the group consisting of hydrogen and an alkyl group having from 1 to 3 carbon atoms.

19. The method according to claim 16 wherein R11, R12, R13, and R14 are each selected from the group consisting of hydrogen, and an alkyl group having from 1 to 3 carbon atoms.

20. The method according to claim 16 wherein R3, R4, R5, and R6 are the same and each is hydrogen.

21. The method according to claim 20 wherein R11, R12, R13, and R14 are the same and each is hydrogen.

22. The method according to claim 21 wherein R1 and R2 are the same and each is methyl.

23. The method according to claim 21 wherein R1 is methyl and R2 is ethyl.

24. The method according to claim 21 wherein R1 and R2 are the same and each is ethyl.

25. The method according to claim 1 wherein the templating agent has a molecular structure of the form:

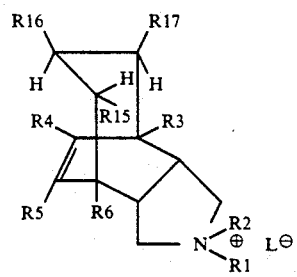

wherein:

R1 and R2 are each selected from the group consisting of hydrogen, a lower alkyl group, and, when taken together, a spirocyclic group having from 3 to 6 carbon atoms;

R3, R4, R5 and R6 are each selected from the group consisting of hydrogen, halogen, and a lower alkyl group;

R15, R16, and R17 are each selected from the group consisting of hydrogen, and a lower alkyl group; and L is an anion.

26. The method according to claim 25 wherein R1 and R2 are selected from the group consisting of hydrogen, an alkyl group having from 1 to 3 carbon atoms, and, when taken together, a spirocyclic group having from 4 to 5 carbon atoms.

27. The method according to claim 25 wherein R3, R4, R5 and R6 are each selected from the group consisting of hydrogen and an alkyl group having from 1 to 3 carbon atoms.

28. The method according to claim 25 wherein R15, R16, and R17 are each selected from the group consisting of hydrogen, and an alkyl group having from 1 to 3 carbon atoms.

29. The method according to claim 25 wherein R3, R4, R5, and R6 are the same and each is hydrogen.

30. The method according to claim 29 wherein R15, R16, and R17 are the same and each is hydrogen.

31. The method according to claim 30 wherein R1 and R2 are the same and each is methyl.

32. The method according to claim 30 wherein R1 is methyl and R2 is ethyl.

33. The method according to claim 1 wherein the templating agent has a molecular structure of the form:

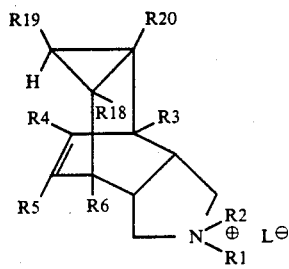

wherein:
R1 and R2 are each selected from the group consisting of hydrogen, a lower alkyl group, and, when taken together, a spirocyclic group having from 3 to 6 carbon atoms;
R3, R4, R5 and R6 are each selected from the group consisting of hydrogen, halogen, and a lower alkyl group;
R18, R19, and R20 are each selected from the group consisting of hydrogen, and a lower alkyl group; and
L is an anion.

34. The method according to claim 33 wherein R1 and R2 are selected from the group consisting of hydrogen, an alkyl group having from 1 to 3 carbon atoms, and, when taken together, a spirocyclic group having from 4 to 5 carbon atoms.

35. The method according to claim 33 wherein R3, R4, R5 and R6 are each selected from the group consisting of hydrogen and an alkyl group having from 1 to 3 carbon atoms.

36. The method according to claim 33 wherein R18, R19, and R20 are each selected from the group consisting of hydrogen, and an alkyl group having from 1 to 3 carbon atoms.

37. The method according to claim 33 wherein R3, R4, R5, and R6 are the same and each is hydrogen.

38. The method according to claim 37 wherein R18, R19, and R20 are the same and each is hydrogen.

39. The method according to claim 38 wherein R1 and R2 are the same and each is methyl.

40. The method according to claim 1 wherein L is selected from the group consisting of fluoride, chloride, bromide, iodide, hydroxide, acetate, sulfate, and carboxylate.

41. The method according to claim 40 wherein L is hydroxide.

42. The method according to claim 1 wherein the trivalent element is selected from the group consisting of aluminum, boron, gallium, iron, and combinations thereof.

43. The method according to claim 42 wherein the trivalent element is selected from the group consisting of aluminum, boron, and combinations thereof.

44. The method according to claim 43 wherein the source of aluminum is Y zeolite.

45. The method according to claim 1 wherein the tetravalent element is selected from the group consisting of silicon, germanium, and combinations thereof.

46. The method according to claim 45 wherein the tetravalent element is silicon.

47. The method according to claim 1 wherein the crystalline material is a molecular sieve.

48. The method according to claim 47 wherein the molecular sieve is a crystalline silicate.

49. The method according to claim 47 wherein the molecular sieve is a crystalline borosilicate.

50. The method according to claim 47 wherein the molecular sieve is a crystalline aluminosilicate zeolite.

51. The method according to claim 47 wherein the molecular sieve is ZSM-12.

52. The method according to claim 47 wherein the molecular sieve is SSZ-13.

53. The method according to claim 47 wherein the molecular sieve is SSZ-15.

54. The method according to claim 47 wherein the molecular sieve is SSZ-31.

55. The method according to claim 47 wherein the molecular sieve is SSZ-33.

56. The method according to claim 47 wherein the molecular sieve is zeolite beta.

57. A crystalline material comprising one or a combination of oxides selected from the group consisting of one or more trivalent element(s) and one or more tetravalent element(s), and having therein the templating agent of claim 1.

58. The crystalline material of claim 57 comprising oxide units and having a molar composition, as synthesized and in the anhydrous state, as follows:

$$aQ:bM_2O:cW_2O_3:100YO_2$$

wherein:
Q is the templating agent;
M is one or a combination of alkali metal cations and/or alkaline earth metal cations;
W is one or a combination of elements selected from aluminum, boron, gallium, and iron;
Y is one or a combination of elements selected from silicon and germanium;
has a value in the range of 5 to 50;
b has a value in the range of 0.5 to 100; and
c has a value in the range of 0 to 10.

59. The composition according to claim 57 wherein the crystalline material is a molecular sieve.

60. The composition according to claim 59 wherein the molecular sieve is a silicate zeolite.

61. The composition according to claim 59 wherein the molecular sieve is a borosilicate zeolite.

62. The composition according to claim 59 wherein the molecular sieve is an aluminosilicate zeolite.

63. The composition according to claim 58 wherein the crystalline material is a molecular sieve.

64. The composition according to claim 63 wherein the molecular sieve is a silicate zeolite.

65. The composition according to claim 63 wherein the molecular sieve is a borosilicate zeolite.

66. The composition according to claim 63 wherein the molecular sieve is an aluminosilicate zeolite.

* * * * *